(12) United States Patent
Hazlebeck et al.

(10) Patent No.: US 7,662,616 B2
(45) Date of Patent: *Feb. 16, 2010

(54) PHOTOSYNTHETIC OIL PRODUCTION WITH HIGH CARBON DIOXIDE UTILIZATION

(75) Inventors: David A. Hazlebeck, El Cajon, CA (US); Eric H. Dunlop, Paradise (AU)

(73) Assignee: General Atomics, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/549,561

(22) Filed: Oct. 13, 2006

(65) Prior Publication Data

US 2008/0090284 A1    Apr. 17, 2008

(51) Int. Cl.
*C12M 1/00* (2006.01)

(52) U.S. Cl. ............... 435/289.1; 435/292.1; 435/257.1; 47/1.4

(58) Field of Classification Search .............. 435/292.1, 435/293.1, 134, 166; 47/1.4
See application file for complete search history.

(56) References Cited

U.S. PATENT DOCUMENTS

| | | | |
|---|---|---|---|
| 2,658,310 A | 11/1953 | Cook | |
| 2,732,661 A | 1/1956 | Spoehr et al. | |
| 2,732,663 A * | 1/1956 | Dewey, II | 47/1.4 |
| 2,854,792 A | 10/1958 | Juda | |
| 2,949,700 A | 8/1960 | Kathrein | |
| 3,108,402 A | 10/1963 | Kathrein | |
| 3,195,271 A | 7/1965 | Golueke et al. | |
| 3,218,758 A | 11/1965 | Konikoff | |
| 3,446,488 A | 5/1969 | Mail et al. | |
| 3,468,057 A | 9/1969 | Buisson et al. | |
| 3,521,400 A | 7/1970 | Ort | |
| 3,955,318 A | 5/1976 | Hulls | |
| 3,958,364 A | 5/1976 | Schenck et al. | |
| 4,087,936 A * | 5/1978 | Savins et al. | 47/1.4 |
| 4,236,349 A | 12/1980 | Ramus | |
| 4,341,038 A * | 7/1982 | Bloch et al. | 47/1.4 |
| 4,417,415 A | 11/1983 | Cysewski et al. | |
| 4,473,970 A * | 10/1984 | Hills | 47/1.4 |
| 4,544,567 A | 10/1985 | Gottesman | |
| 4,958,460 A | 9/1990 | Nielson et al. | |
| 5,330,913 A | 7/1994 | Nakayama | |
| 5,951,875 A | 9/1999 | Kanel et al. | |
| 6,000,551 A | 12/1999 | Kanel et al. | |

(Continued)

OTHER PUBLICATIONS

NREL/TP-580-24190, A Look Back at the U.S. Department of Energy's Aquatic Species Program; Biodiesel from Algae, Jul. 1998.

(Continued)

*Primary Examiner*—William H Beisner
(74) *Attorney, Agent, or Firm*—Nydegger & Associates

(57) ABSTRACT

A system for processing oil from algae is disclosed. Specifically, the system recycles byproducts of the process for use as nutrients during algae growth and oil production. The system includes a conduit for growing algae and an algae separator that removes the algae from the conduit. Also, the system includes a device for lysing the algae and an oil separator to remove the oil from the lysed matter. Further, the system includes a biofuel reactor that receives oil from the oil separator and synthesizes biofuel and glycerin. Moreover, the algae separator, oil separator and biofuel reactor all recycle byproducts back to the conduit to support further algae growth.

12 Claims, 1 Drawing Sheet

U.S. PATENT DOCUMENTS

| | | |
|---|---|---|
| 6,524,486 B2 | 2/2003 | Borodyanski et al. |
| 6,667,171 B2 | 12/2003 | Bayless et al. |
| 2007/0232818 A1* | 10/2007 | Crawford et al. ............ 554/174 |
| 2008/0086938 A1* | 4/2008 | Hazlebeck et al. ............ 47/1.4 |

OTHER PUBLICATIONS

Miao et al., Bioresource Technology, Biodiesel production from heterotrophic microalgal oil, Apr. 2006, vol. 97, p. 841-846.

Medina et al., Biotechnology Advances, Downstream Processing of Algal Polyunsaturated Fatty Acids, 1998, vol. 16, No. 3, (see p. 526, 3rd paragraph) Only pp. 517 and 526.

Spolaore et al., Journal of Bioscience & Biotechnology, Commercial Applications of Microalgae, Feb. 2006, vol. 101, No. 2, p. 87-96.

Barbosa et al., Biomolecular Engineering, Optimisation of cultivation parameters in photobioreactors for microalgae cultivation using the A-stat technique, 2003, vol. 20, p. 115-123. (see abstract).

* cited by examiner

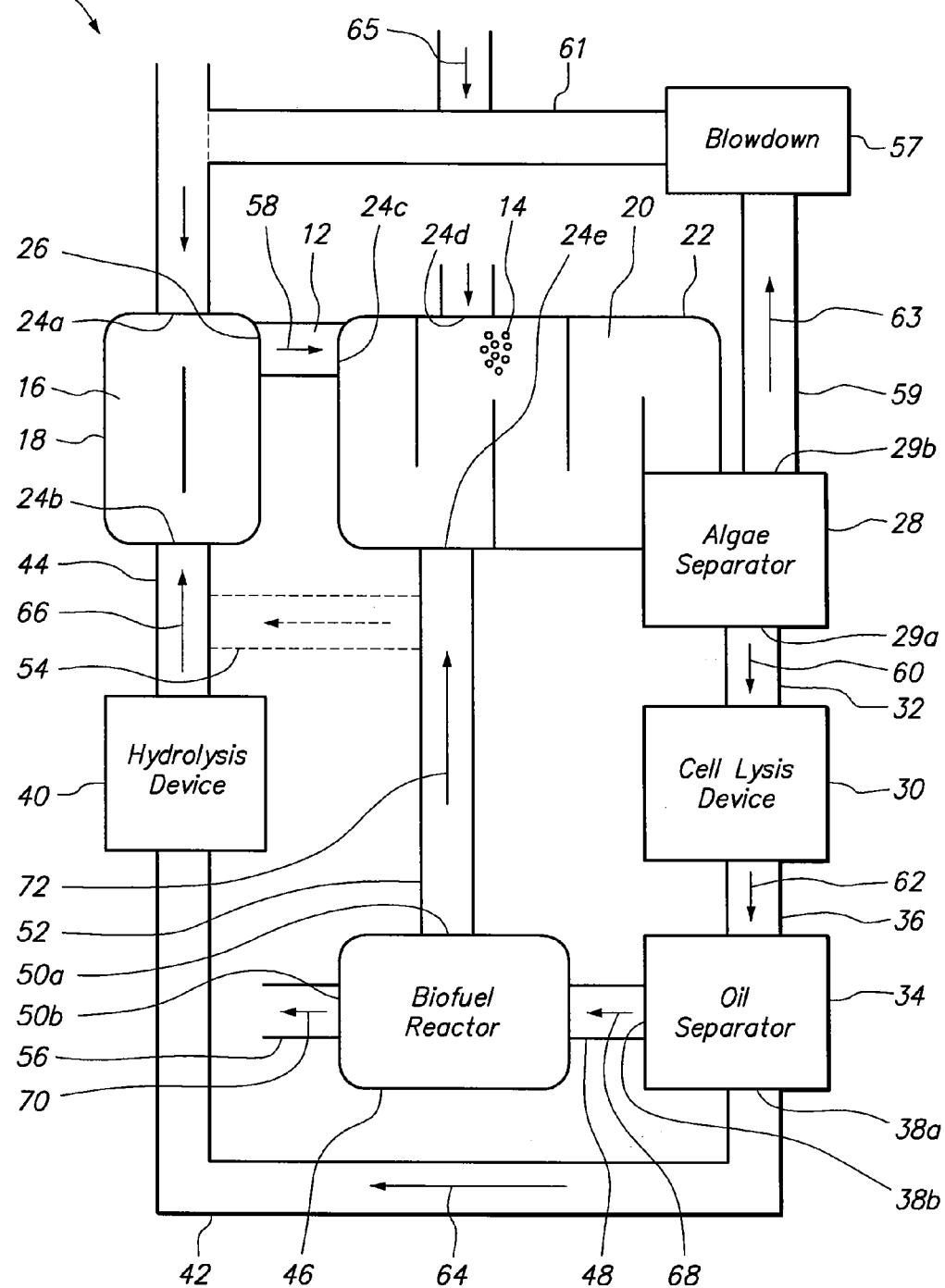
FIGURE

PHOTOSYNTHETIC OIL PRODUCTION WITH HIGH CARBON DIOXIDE UTILIZATION

FIELD OF THE INVENTION

The present invention pertains generally to processes for harvesting oil from algae. More particularly, the present invention pertains to a cost efficient supply of nutrients to support the growth of algae cells having a high oil content. The present invention is particularly, but not exclusively, useful as a system and method for recycling byproducts of an algae oil harvesting process for use in supporting algae cell growth and oil production.

BACKGROUND OF THE INVENTION

As worldwide petroleum deposits decrease, there is rising concern over shortages and the costs that are associated with the production of hydrocarbon products. As a result, alternatives to products that are currently processed from petroleum are being investigated. In this effort, biofuels such as biodiesel have been identified as a possible alternative to petroleum-based transportation fuels. In general, biodiesel is a fuel comprised of mono-alkyl esters of long chain fatty acids derived from plant oils or animal fats. In industrial practice, biodiesel is created when plant oils or animal fats are reacted with an alcohol, such as methanol.

For plant-derived biofuel, solar energy is first transformed into chemical energy through photosynthesis. The chemical energy is then refined into a usable fuel. Currently, the process involved in creating biofuel from plant oils is expensive relative to the process of extracting and refining petroleum. It is possible, however, that the cost of processing a plant-derived biofuel could be reduced by maximizing the rate of growth of the plant source. Because algae is known to be one of the most efficient plants for converting solar energy into cell growth, it is of particular interest as a biofuel source. However, current algae processing methods have failed to result in a cost effective algae-derived biofuel.

In overview, the biochemical process of photosynthesis provides algae with the ability to convert solar energy into chemical energy. During cell growth, this chemical energy is used to drive synthetic reactions, such as the formation of sugars or the fixation of nitrogen into amino acids for protein synthesis. Excess chemical energy is stored in the form of fats and oils as triglycerides. Thus, the creation of oil in algae only requires sunlight, carbon dioxide and the nutrients necessary for formation of triglycerides. Nevertheless, with the volume requirements for a fuel source, the costs associated with the inputs are high.

In light of the above, it is an object of the present invention to provide a system and method for processing oil from algae which reduces input costs. For this purpose, a number of systems have been developed, such as those disclosed in co-pending U.S. patent application Ser. No. 11/549,532 for an invention entitled "Photosynthetic Oil Production in a Two-Stage Reactor," co-pending U.S. patent application Ser. No. 11/549,541 for an invention entitled "Photosynthetic Carbon Dioxide Sequestration and Pollution Abatement" and co-pending U.S. patent application Ser. No. 11/549,552 for an invention entitled "High Photoefficiency Microalgae Bioreactors," which are filed concurrently herewith and assigned to the same assignee as the present invention, and are hereby incorporated by reference. Another object of the present invention is to provide a recycling system for feeding oil harvesting byproducts back to the conduit where high oil content algae is grown. Still another object of the present invention is to provide a system for supplying nutrients to algae cells in the form of processed algae cell matter. Another object of the present invention is to provide a system for recycling the glycerin byproduct from the creation of biofuel as a source of carbon to foster further oil production in algae cells. Another object of the present invention is to provide a system for processing oil from algae that defines a flow path for continuous movement of the algae and its processed derivatives. Yet another object of the present invention is to provide a system and method for processing algae with high oil content that is simple to implement, easy to use, and comparatively cost effective.

SUMMARY OF THE INVENTION

In accordance with the present invention, a system is provided for efficiently processing oil from algae. For this purpose, the system recycles byproducts of the process for use as nutrients to support algae cell growth and the cellular production of oil. Structurally, the system includes a chemostat that defines a conduit for growing algae cells. The chemostat's conduit includes input ports for feeding material into the conduit as well as an output port. Further, the system includes a plug flow reactor that defines a conduit for fostering oil production within the algae cells. For the present invention, the plug flow reactor has an input port that is positioned to receive material from the output port of the chemostat.

In addition to the chemostat and plug flow reactor, the system includes an algae separator. Specifically, the algae separator is positioned in fluid communication with the plug flow reactor to remove the algae cells from the plug flow reactor's conduit. Structurally, the algae separator includes an outlet for the remaining effluence which is in fluid communication with the input port of the chemostat. Further, the system includes a device for lysing algae cells to unbind oil from the algae cells. For purposes of the present invention, the lysing device is positioned to receive algae cells from the algae separator.

Downstream of the lysing device, the system includes an oil separator that receives the lysed cells and withdraws the oil from remaining cell matter. For purposes of the present invention, the oil separator has an outlet for the remaining cell matter which is in fluid communication with the input port of the chemostat. Further, the system may include a hydrolyzing device interconnected between the oil separator and the chemostat. In addition to the cell matter outlet, the oil separator includes an outlet for the oil. For the present invention, the system includes a biofuel reactor that is in fluid communication with the outlet for oil. In a known process, the biofuel reactor reacts an alcohol with the oil to synthesize biofuel and, as a byproduct, glycerin. Structurally, the biofuel reactor includes an exit for the glycerin that is in fluid communication with the input port of the plug flow reactor.

In operation, algae cells are grown in the chemostat and are continuously transferred to the plug flow reactor. In the plug flow reactor, the algae cells increase the rate of intracellular oil production. Thereafter, the algae separator removes the algae cells from the remaining effluence in the plug flow reactor. The remaining effluence is diverted back to the chemostat to serve as a source of nutrition for the algae cells growing therein while the algae cells are delivered to the cell lysis device. At the cell lysis device, the cells are lysed to unbind the oil from the remaining cell matter. This unbound cell material is received by the oil separator from the cell lysis device. Next, the oil separator withdraws the oil from the remaining cell matter and effectively forms two streams of material. The stream of remaining cell matter is transferred to the hydrolysis device where the cell matter is broken into small units which are more easily absorbed by algae cells during cell growth. Thereafter, the hydrolyzed cell matter is delivered to the chemostat to serve as a source of nutrition for the algae cells growing therein. At the same time, the stream of oil is transmitted from the oil separator to the biofuel reactor. In the biofuel reactor, the oil is reacted with an alcohol to form biofuel and a glycerin byproduct. The glycerin byproduct is fed back into the plug flow reactor to serve as a source of carbon for the algae cells therein during the production of intracellular oil.

BRIEF DESCRIPTION OF THE DRAWINGS

The novel features of this invention, as well as the invention itself, both as to its structure and its operation, will be best understood from the accompanying drawing, taken in conjunction with the accompanying description, in which the FIGURE is a schematic view of the system for processing oil from algae in accordance with the present invention.

DESCRIPTION OF THE PREFERRED EMBODIMENTS

Referring to the FIGURE, a system for processing oil from algae in accordance with the present invention is shown and generally designated 10. Specifically, in the system 10 byproducts of the processing method are recycled to foster growth of algae cells having high oil content. As shown, the system 10 includes a conduit 12 for growing algae cells with high oil content (exemplary cells depicted at 14). As further shown, the conduit 12 includes an upstream conduit section 16 that is defined by a continuously stirred first stage reactor or chemostat 18. Also, the conduit 12 includes a downstream conduit section 20 that is defined by a plug flow second stage reactor 22. As shown, each conduit section 16, 20 includes input ports 24a-e. Further, the upstream conduit section 16 includes an output port 26. As shown, the output port 26 of the upstream conduit section 16 and the input port 24c of the plug flow reactor 22 are in fluid communication. In this manner, the conduit 12 passes through the chemostat 18 and the plug flow reactor 22.

As further shown in the FIGURE, the system 10 includes an algae separator 28 that is in fluid communication with the downstream conduit section 20 in the plug flow reactor 22. For purposes of the present invention, the algae separator 28 removes algae cells 14 from the downstream conduit section 20. As shown, the algae separator includes outlets 29a and 29b. Also, the system 10 includes a cell lysis device 30 that receives algae cells 14 from the outlet 29a of the algae separator 28 via pipe 32. As shown, the cell lysis device 30 is in fluid communication with an oil separator 34. Specifically, a pipe 36 interconnects the cell lysis device 30 and the oil separator 34. For purposes of the present invention, the oil separator 34 is provided with two outlets 38a-b. As shown, the outlet 38a is connected to a hydrolysis device 40 by a pipe 42. Further, the hydrolysis device 40 is connected to the input port 24b in the upstream conduit section 16 of the chemostat 18 by a pipe 44.

Referring back to the oil separator 34, it can be seen that the outlet 38b is connected to a biofuel reactor 46 by a pipe 48. It is further shown that the biofuel reactor 46 includes two exits 50a-b. For purposes of the present invention, the exit 50a is connected to the input port 24e in the downstream conduit section 20 of the plug flow reactor 22 by a pipe 52. Additionally or alternatively, the exit 50a may be connected to the input port 24b in the upstream conduit section 16 of the chemostat 18 by a pipe 54 (shown in phantom). As further shown, the exit 50b is connected to a pipe 56 which may connect to a tank or reservoir (not shown) for purposes of the present invention.

Referring now to the algae separator 28, it can be seen that the outlet 29b is in fluid communication with the input port 24a of the chemostat 18. Further, a blowdown 57 is shown to be interconnected between the algae separator 28 and the input port 24a. Specifically, a pipe 59 connects the outlet 29b and the blowdown 57, and a pipe 61 connects the blowdown 57 and the input port 24a.

In operation of the present invention, algae cells 14 are initially grown in the upstream conduit section 16 in the chemostat 18. Specifically, a medium with a nutrient mix is continuously fed through input port 24a into the upstream conduit section 16 at a selected rate. Further, the conditions in the upstream conduit section 16 are maintained for maximum algal growth. For instance, in order to maintain the desired conditions, the medium and the algae cells 14 are moved around the upstream conduit section 16 at a fluid flow velocity in the range of approximately ten to two hundred centimeters per second, and preferably at fifty centimeters per second. Further, the amount of algae cells 14 in the upstream conduit section 16 is kept substantially constant. Specifically, the medium with nutrient mix is continuously fed into the input port 24a and an effluence 58 containing algae cells 14 is continuously removed through the output port 26 of the upstream conduit section 16 as overflow. Under preferred conditions, approximately ten grams of algae per liter of fluid circulate in the upstream conduit section 16. Preferably, the residence time for algae cells 14 in the upstream conduit section 16 is about one to ten days.

After entering the input port 24c, the effluence 58 containing algae cells 14 moves through the downstream conduit section 20 in the direction of arrows 60 in a plug flow regime. Preferably, the effluence 58 moves through the downstream conduit section 20 of the plug flow reactor 22 at a rate of between ten and two hundred centimeters per second. Further, as the effluence 58 moves downstream, a modified nutrient mix may be added to the downstream conduit section 20 through the input port 24d. This modified nutrient mix may contain a limited amount of a selected constituent, such as nitrogen or phosphorous. The absence or small amount of the selected constituent causes the algae cells 14 to focus on energy storage rather than growth. As a result, the algae cells 14 form triglycerides.

At the end of the downstream conduit section 20, the algae separator 28 removes the algae cells 14 from the effluence 58. To facilitate this process, the depth of the downstream conduit section 20 may be increased near the algae separator 28. The corresponding increase in the fluid flow cross-sectional area, and decrease in fluid flow rate, allows the algae cells 14 to settle to the bottom or float to the top of the conduit section 20, depending on the oil content of the algae cells 14. In certain embodiments, the modified nutrient mix may include a limited amount of a predetermined constituent to trigger flocculation of the algae cells 14 in the downstream conduit section 20. The predetermined constituent may be the same as the selected constituent such that a shortage of nitrogen, for example, causes both the production of triglycerides and the flocculation of the algae cells 14.

After the algae cells 14 are removed from the conduit 12 by the algae separator 28, the remaining effluence (indicated by arrow 63) is discharged from the algae separator 28 through the outlet 29b. As shown, the remaining effluence 63 passes through the blowdown 57 where impurities, such as salt, are removed. Then, additional nutrients (indicated by arrow 65) may be added to the remaining effluence 63 for replenishment to support further cell growth in the chemostat 18. After being replenished, the remaining effluence 63 is fed back into the chemostat 18 through the input port 24a.

While the remaining effluence 63 is discharged through outlet 29b, the algae cells 14 removed by the algae separator 28 are delivered to the cell lysis device 30. Specifically, the algae cells 14 pass through the outlet 29a and the pipe 32 to the cell lysis device 30 as indicated by arrow 60. For purposes of the present invention, the cell lysis device 30 lyses the algae cells 14 to unbind the oil therein from the remaining cell matter. After the lysing process occurs, the unbound oil and remaining cell matter, collectively identified by arrow 62, are passed through pipe 36 to the oil separator 34. Thereafter, the oil separator 34 withdraws the oil from the remaining cell matter as is known in the art. After this separation is performed, the oil separator 34 discharges the remaining cell matter (identified by arrow 64) out of the outlet 38a and through the pipe 42 to the input port 24b of the chemostat 18.

In the chemostat 18, the remaining cell matter 64 is utilized as a source of nutrients and energy for the growth of algae cells 14. Because small units of the remaining cell matter 64 are more easily absorbed or otherwise processed by the growing algae cells 14, the remaining cell matter 64 may first be broken down before being fed into the input port 24b of the chemostat 18. To this end, the hydrolysis device 40 is interconnected between the oil separator 34 and the chemostat 18. Accordingly, the hydrolysis device 40 receives the remaining cell matter 64 from the oil separator 34, hydrolyzes the received cell matter 64, and then passes hydrolyzed cell matter (identified by arrow 66) to the chemostat 18 through pipe 44.

Referring back to the oil separator 34, it is recalled that the remaining cell matter 64 was discharged through the outlet 38a. At the same time, the oil withdrawn by the oil separator 34 is discharged through the outlet 38b. Specifically, the oil (identified by arrow 68) is delivered to the biofuel reactor 46 through the pipe 48. In the biofuel reactor 46, the oil 68 is reacted with alcohol, such as methanol, to create mono-alkyl esters, i.e., biofuel fuel. This biofuel fuel (identified by arrow 70) is released from the exit 50b of the biofuel reactor 46 through the pipe 56 to a tank, reservoir, or pipeline (not shown) for use as fuel. In addition to the biofuel fuel 70, the reaction between the oil 68 and the alcohol produces glycerin as a byproduct. For purposes of the present invention, the glycerin (identified by arrow 72) is pumped out of the exit 50a of the biofuel reactor 46 through the pipe 52 to the input port 24c of the plug flow reactor 22.

In the plug flow reactor 22, the glycerin 72 is utilized as a source of carbon by the algae cells 14. Importantly, the glycerin 72 does not provide any nutrients that may be limited to induce oil production by the algae cells 14 or to trigger flocculation. The glycerin 72 may be added to the plug flow reactor 22 at night to aid in night-time oil production. Further, because glycerin 72 would otherwise provide bacteria and/or other non-photosynthetic organisms with an energy source, limiting the addition of glycerin 72 to the plug flow reactor 22 only at night allows the algae cells 14 to utilize the glycerin 72 without facilitating the growth of foreign organisms. As shown in the FIGURE, the exit 50a of the biofuel reactor 46 may also be in fluid communication with the input port 24b of the chemostat 18 via the pipe 54 (shown in phantom). This arrangement allows the glycerin 72 to be provided to the chemostat 18 as a carbon source.

While the particular Photosynthetic Oil Production with High Carbon Dioxide Utilization as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for processing oil from algae which comprises:
   a conduit for growing algae cells with high oil content, said conduit having an input port;
   an algae separator in fluid communication with the conduit for removing the algae cells from remaining effluence, with the remaining effluence being a byproduct;
   a device for lysing the algae cells removed from the conduit to unbind oil within the algae cells;
   an oil separator for withdrawing the oil from remaining cell matter, with the remaining cell matter being a byproduct;
   a reactor for receiving the oil from the oil separator and for synthesizing biofuel and glycerin from said oil, with said glycerin being a byproduct, wherein said reactor has an exit in fluid communication with the input port of the conduit for recycling the glycerin to the conduit to support growth of high oil content algae cells; and
   a means for recycling at least one byproduct through the input port to the conduit to support growth of algae cells with high oil content.

2. A system as recited in claim 1 wherein said algae separator has an outlet in fluid communication with the input port of the conduit for recycling the remaining effluence to the conduit to support growth of high oil content algae cells.

3. A system as recited in claim 1 wherein said oil separator has an outlet in fluid communication with the input port of the conduit for recycling the remaining cell matter to the conduit to support growth of high oil content algae cells.

4. A system as recited in claim 3 wherein the remaining cell matter includes biopolymers, and the system further comprises a means for hydrolyzing the remaining cell matter to reduce the biopolymers therein to smaller subunits, with said hydrolyzing means being interconnected between the outlet of the separator and the input port of the conduit.

5. A system as recited in claim 1 wherein the conduit includes a first conduit section formed in a chemostat for growing algae cells therein, with the first conduit section including a first input port, and further wherein said oil separator has an outlet in fluid communication with the first input port for recycling the remaining cell matter to the first conduit section to support growth of algae cells therein.

6. A system as recited in claim 1 wherein the conduit includes a first conduit section formed in a chemostat for growing algae cells therein, with the first conduit section including a first input port, and further wherein said reactor has an exit in fluid communication with the first input port for recycling the glycerin to the first conduit section to support growth of algae cells therein.

7. A system as recited in claim 1 wherein the conduit includes a second conduit section formed in a plug flow reactor for increasing the oil content of the algae cells therein, with the second conduit section including a second input port, and further wherein said reactor has an exit in fluid communication with the second input port for recycling the glycerin to the second conduit section to support oil production within the algae cells therein.

8. A system for processing oil from algae which comprises:
   a conduit for growing algae cells with high oil content, said conduit having an input port;

an algae separator in fluid communication with the conduit for removing the algae cells from remaining effluence, with the remaining effluence being a byproduct;

a device for lysing the algae cells removed from the conduit to unbind oil from the algae cells;

an oil separator for withdrawing the oil from remaining cell matter, said oil separator having an outlet in fluid communication with the input port of the conduit for recycling the remaining cell matter to the conduit to support growth of high oil content algae cells; and a means for hydrolyzing the remaining cell matter to reduce the remaining cell matter to smaller subunits, with said hydrolyzing means being interconnected between the outlet of the separator and the input port of the conduit.

9. A system as recited in claim 8 further comprising:

a reactor for receiving the oil from the oil separator and for synthesizing biofuel and glycerin from said oil, said reactor having an exit in fluid communication with the input port of the conduit for recycling the glycerin to the conduit to support growth of high oil content algae cells.

10. A system as recited in claim 9 wherein the conduit includes a first conduit section formed in a chemostat for growing algae cells therein, with said first conduit section including the input port, and further wherein said outlet of said oil separator is in fluid communication with the input port of the first conduit section for recycling the remaining cell matter to the first conduit section to support growth of algae cells therein.

11. A system as recited in claim 10 wherein said exit of said reactor is in fluid communication with the input port of the first conduit section for recycling the glycerin to the first conduit section to support growth of algae cells therein.

12. A system as recited in claim 10 wherein the conduit includes a second conduit section formed in a plug flow reactor for increasing the oil content of the algae cells therein, with said second conduit section including an input port, and further wherein said exit of said reactor is in fluid communication with the input port in the second conduit section for recycling the glycerin to the second conduit section to support oil production within the algae cells therein.

* * * * *